US012613226B2

(12) United States Patent
Noda

(10) Patent No.: US 12,613,226 B2
(45) Date of Patent: Apr. 28, 2026

(54) PEAK AREA DISPLAY DEVICE, PEAK AREA DISPLAY METHOD, PEAK AREA CALCULATION DEVICE AND PEAK AREA CALCULATION METHOD

(71) Applicant: Shimadzu Corporation, Kyoto (JP)

(72) Inventor: Akira Noda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 200 days.

(21) Appl. No.: 17/966,557

(22) Filed: Oct. 14, 2022

(65) Prior Publication Data

US 2023/0126478 A1     Apr. 27, 2023

(30) Foreign Application Priority Data

Oct. 21, 2021     (JP) ................................. 2021-172659

(51) Int. Cl.
*G01N 30/86* (2006.01)
*G01N 33/15* (2006.01)
G01N 30/02 (2006.01)

(52) U.S. Cl.
CPC ......... *G01N 30/8631* (2013.01); *G01N 33/15* (2013.01); *G01N 2030/027* (2013.01)

(58) Field of Classification Search
CPC ............... G01N 30/8631; G01N 33/15; G01N 2030/027; G01N 30/86; G01N 30/8634; G01N 30/8637; G01N 2030/025
USPC ....... 73/1.02, 23.36, 61.52, 149; 422/70, 89; 96/101; 95/82; 702/85, 104; 210/756
See application file for complete search history.

(56) References Cited

U.S. PATENT DOCUMENTS

2023/0097148 A1 * 3/2023 Fujita ..................... G01N 30/86
702/22

FOREIGN PATENT DOCUMENTS

CN      114034806 A   *   2/2022   ............. G01N 30/02
CN      114384181 A   *   4/2022

OTHER PUBLICATIONS

"I-PDeA II Intelligent Peak Deconvolution Analysis II", Shimadzu Corporation, searched on Sep. 15, 2021, submitted with a machine translation.
"Peak Fit", Hulinks Inc. Website: https://www.hulinks.co.jp/software/da_visual/peakfit/functions#chorom, searched on Jun. 4, 2021.

(Continued)

*Primary Examiner* — Robert R Raevis
(74) *Attorney, Agent, or Firm* — Muir Patent Law, PLLC

(57) ABSTRACT

A peak area display device includes an acquirer, a peak area calculator and a display device. The acquirer acquires measurement data measured by a chromatograph. A peak area calculator fits a model function to a chromatogram by performing optimization calculation to maximize or minimize a peak area while keeping a value to be taken by a loss function representing a residual between the chromatogram obtained from the measurement data MD and the model function in a predetermined range. The peak area calculator obtains a maximum value or a minimum value of the peak area. A display device (display) displays the maximum value or the minimum value of the peak area obtained by the peak area calculator, or information obtained by a process of the maximum value or the minimum value of the peak area.

13 Claims, 12 Drawing Sheets

RESIDUAL OBTAINED BY UPPER BOUND ESTIMATION(CH2)

——— RESIDUAL OBTAINED BY UPPER BOUND ESTIMATION(CH2)       - - - PEAK(CH2)

(56) References Cited

OTHER PUBLICATIONS

Akbari et al. "Known-value constraint in multivariate curve resolution", Analytica Chimica Acta, vol. 1030, Nov. 7, 2018.

Arase et al., "Intelligent peak deconvolution through in-depth study of the data matrix from liquid chromatography coupled with a photo-diode array detector applied to pharmaceutical analysis" Journal of Chromatography A, vol. 1469, Oct. 2016.

Betancourt, "A Conceptual Introduction to Hamiltonian Monte Carlo", Jul. 16, 2018.

Moussaoui et al., "Bayesian analysis of spectral mixture data using Markov Chain Monte Carlo Methods", Journal article, Chemometrics and Intelligent Laboratory Systems, vol. 81, issue 2, pp. 137-148, Apr. 2006.

Office Action dated Aug. 30, 2024, in the counterpart Chinese patent application No. 202211259684.8.

Notice of Reasons for Refusal dated May 27, 2025, in the counterpart Japanese patent application No. 2021-172659.

* cited by examiner

F I G. 1
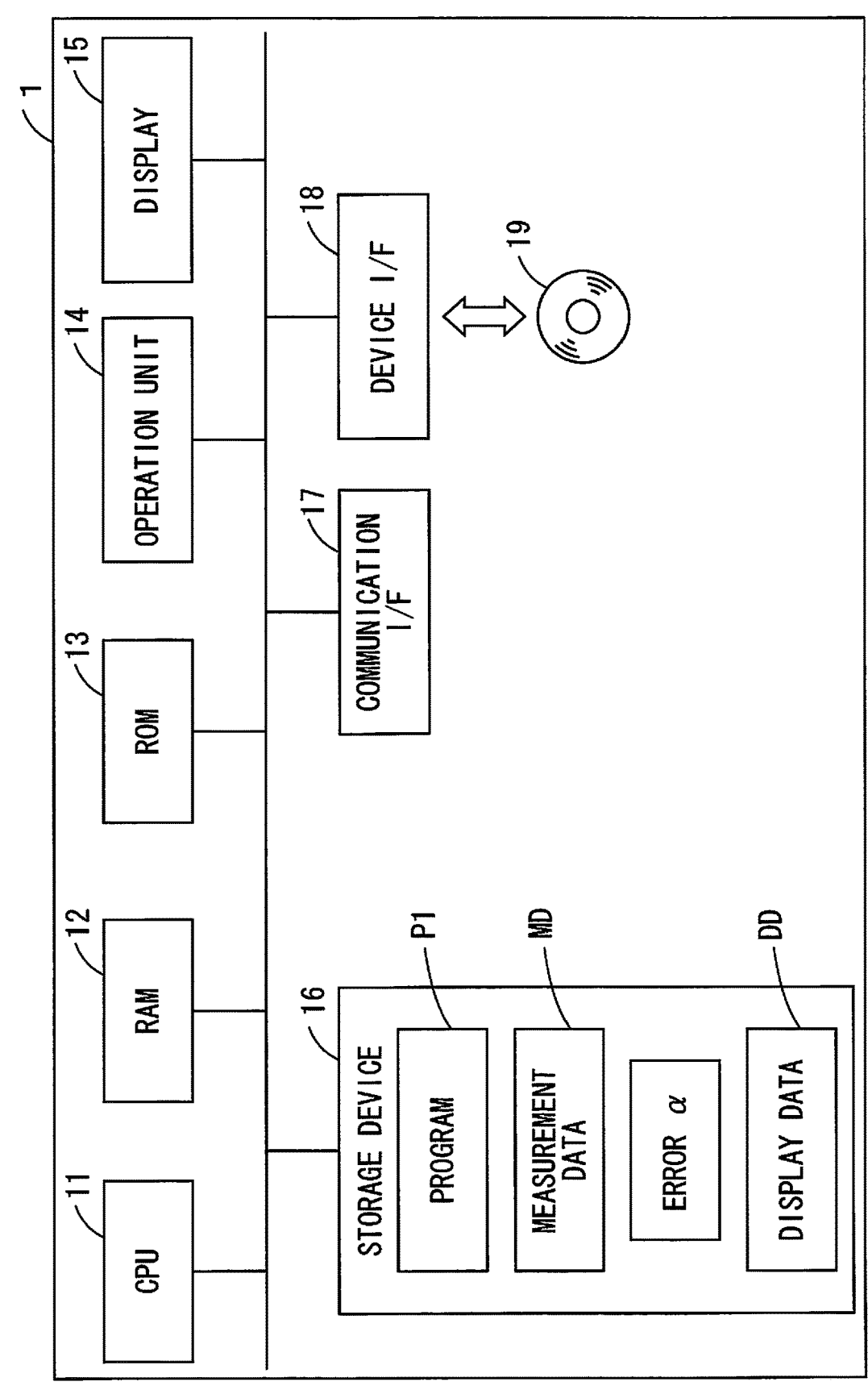

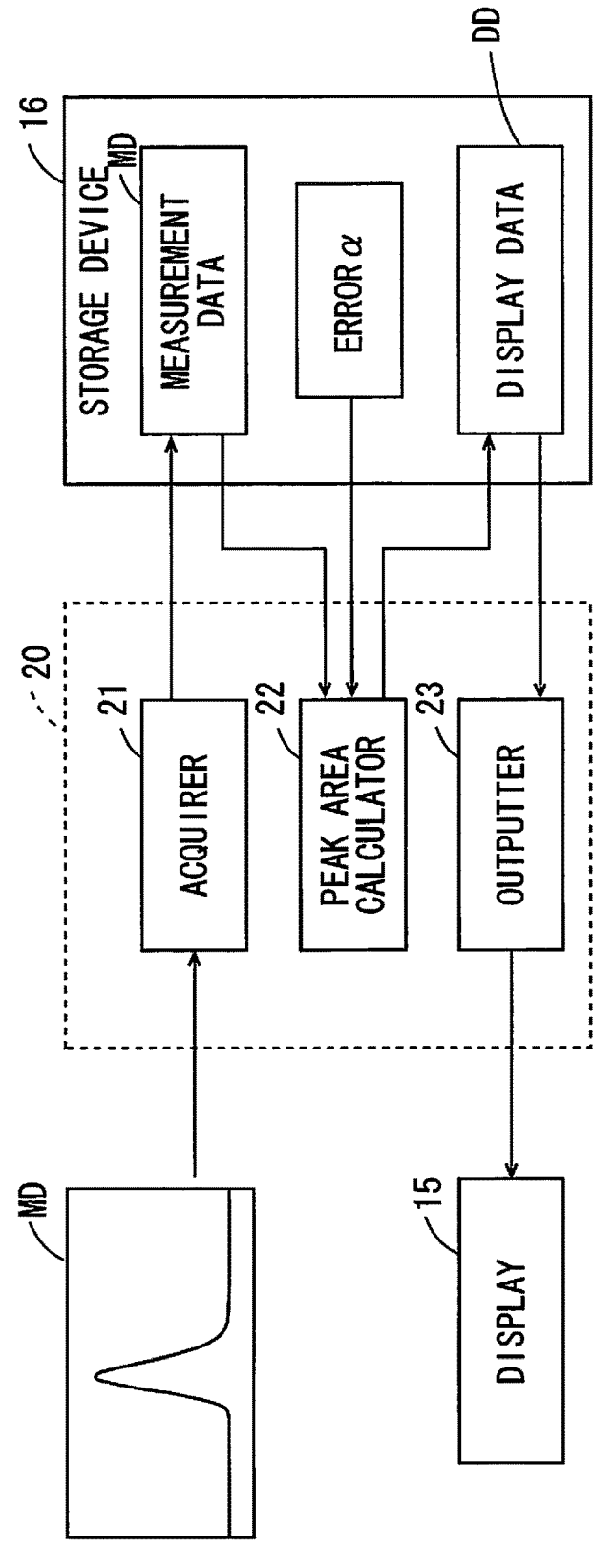
F I G. 2

F I G. 3
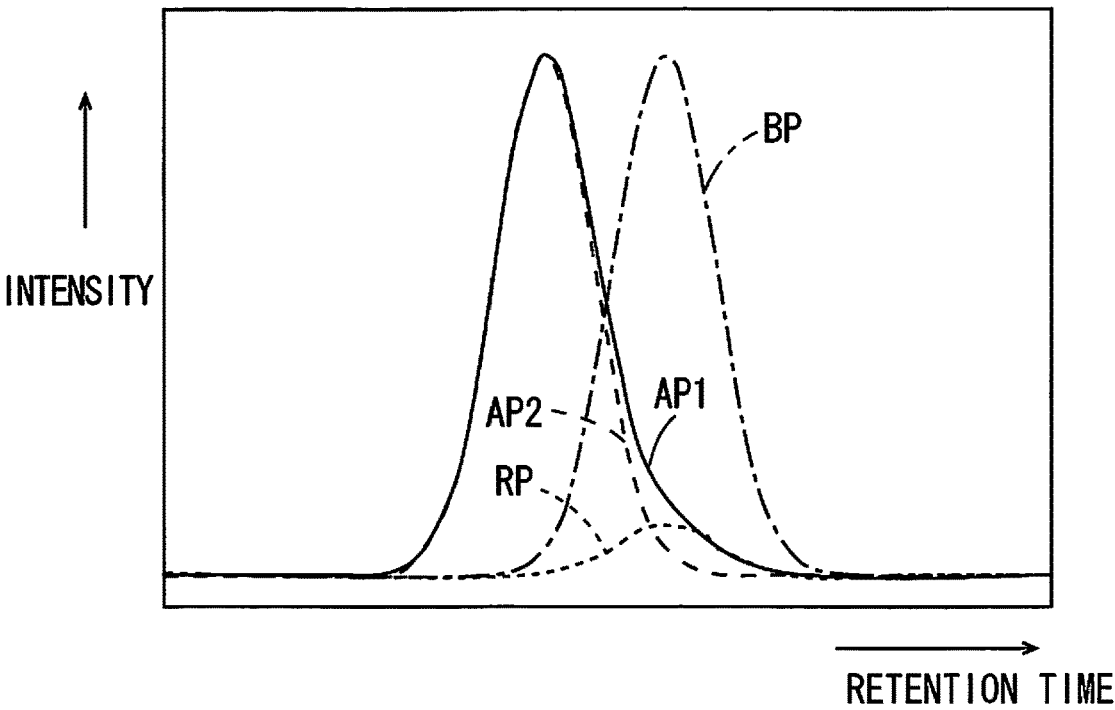
F I G. 4
MEASUREMENT DATA (CH1)
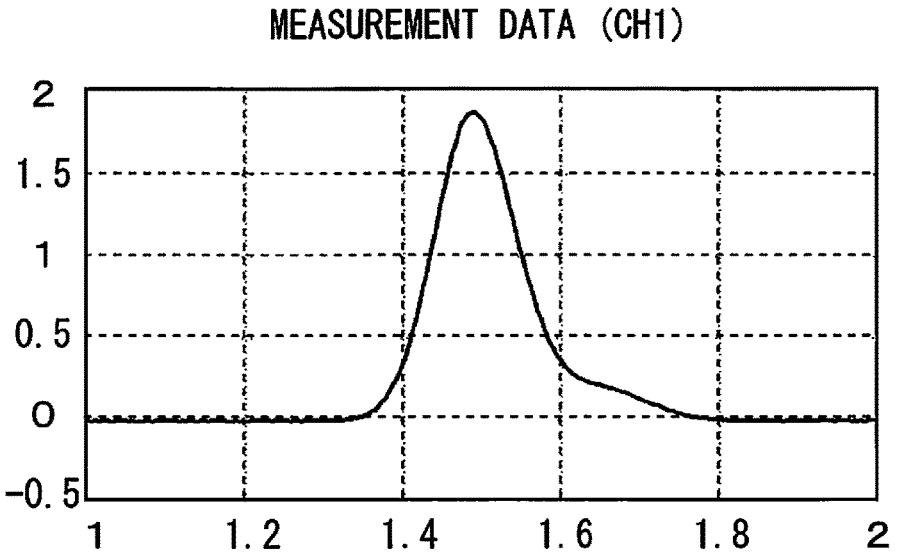

F I G. 5
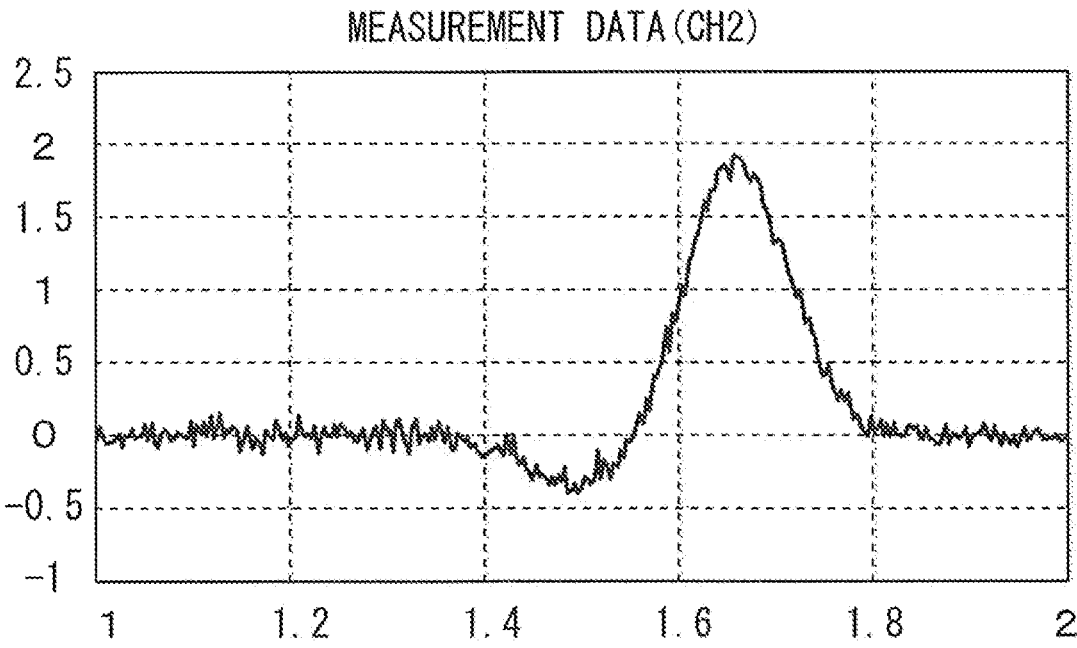
F I G. 6
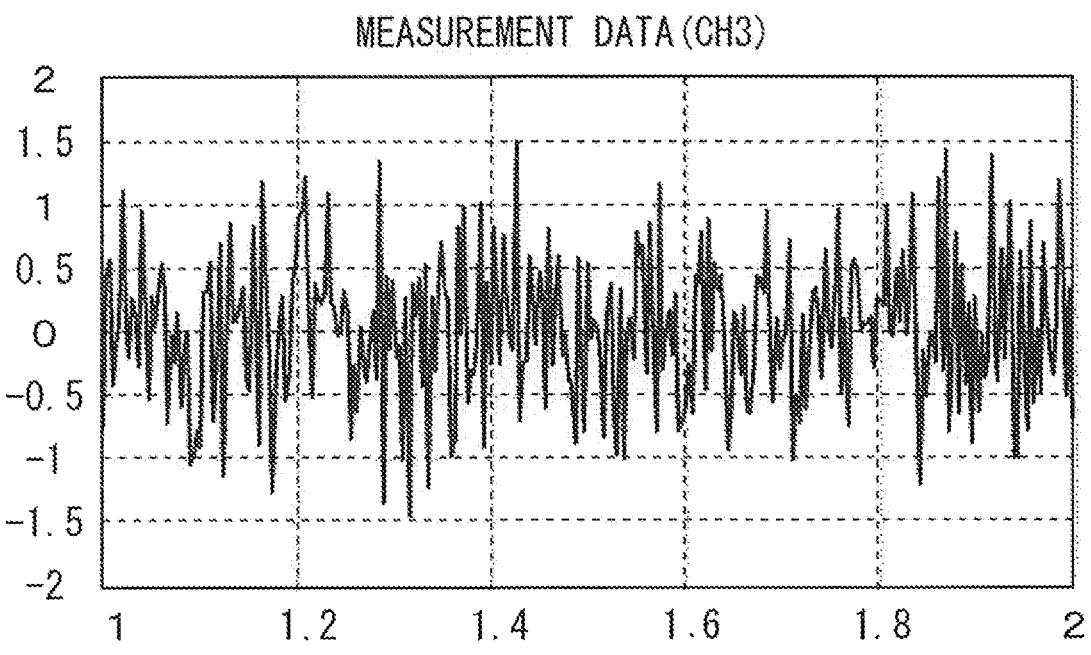

F I G. 7
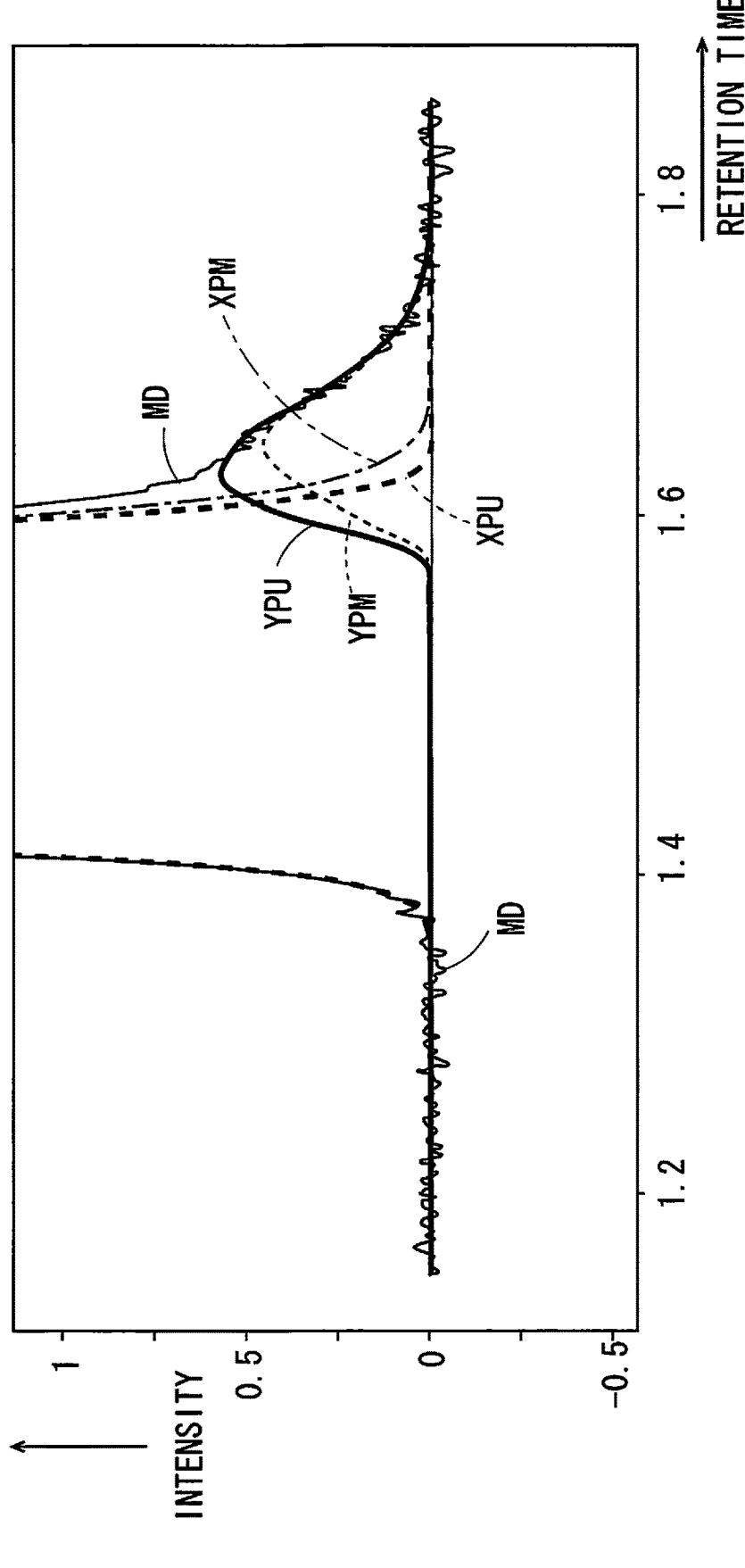

F I G. 8
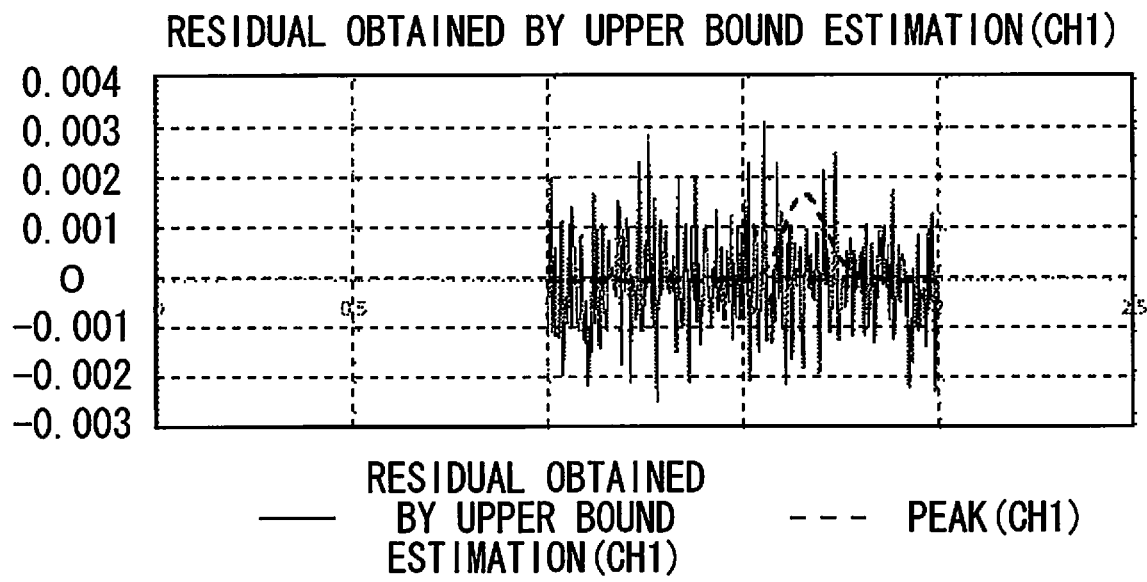
RESIDUAL OBTAINED BY UPPER BOUND ESTIMATION(CH1)
—— RESIDUAL OBTAINED BY UPPER BOUND ESTIMATION(CH1)     - - - PEAK(CH1)
F I G. 9
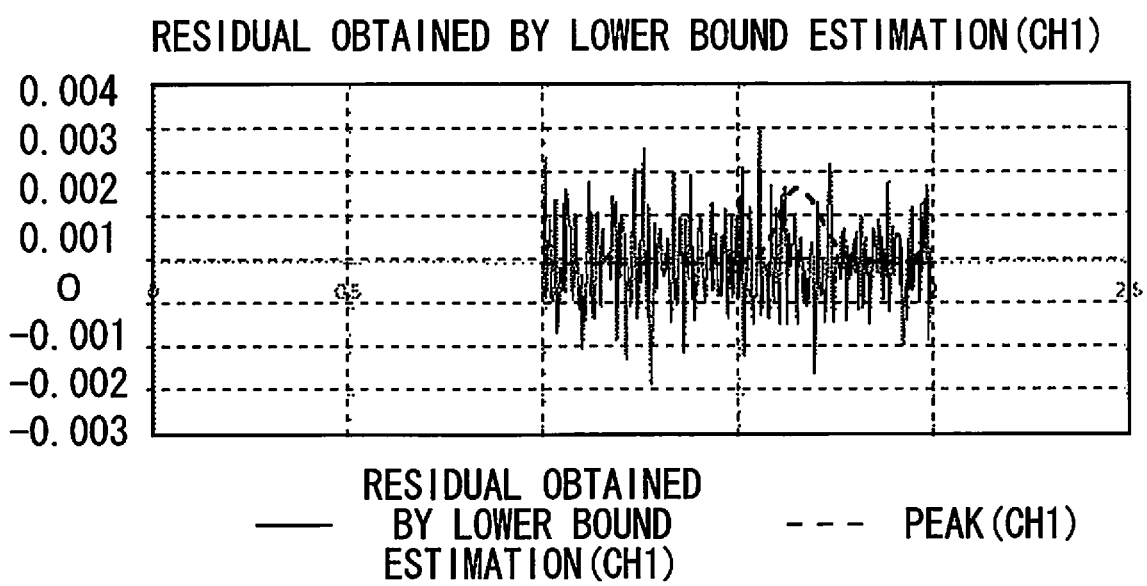
RESIDUAL OBTAINED BY LOWER BOUND ESTIMATION(CH1)
—— RESIDUAL OBTAINED BY LOWER BOUND ESTIMATION(CH1)     - - - PEAK(CH1)

F I G.  1 0
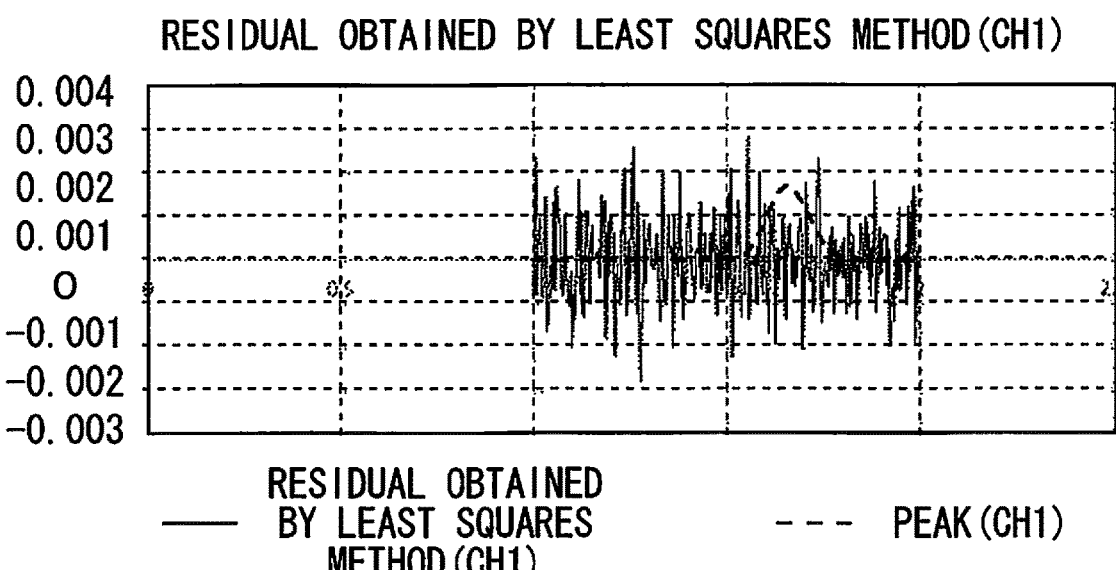
F I G.  1 1
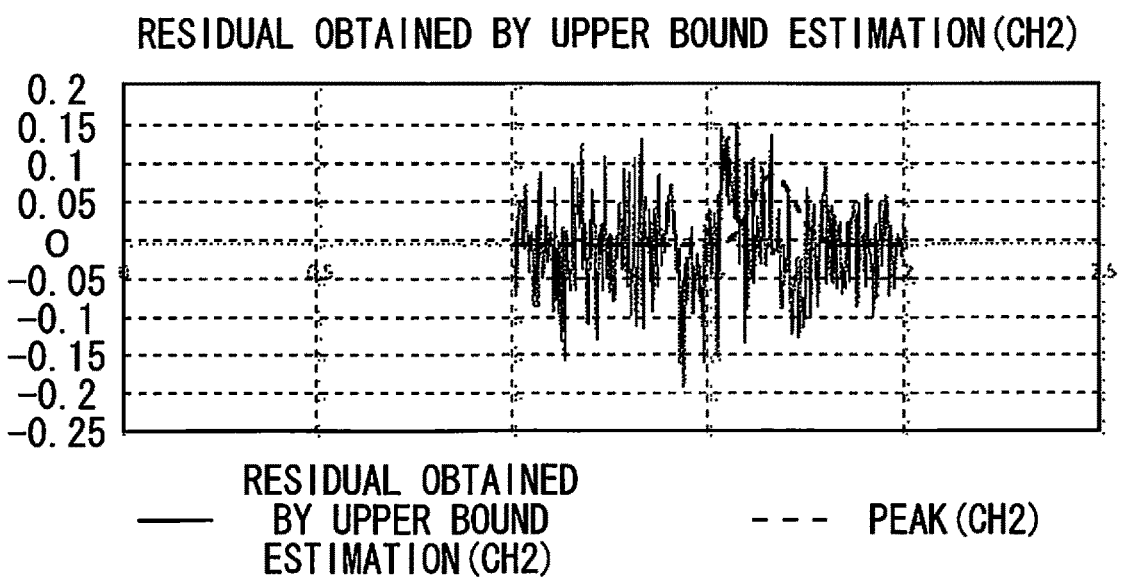

F I G. 1 2
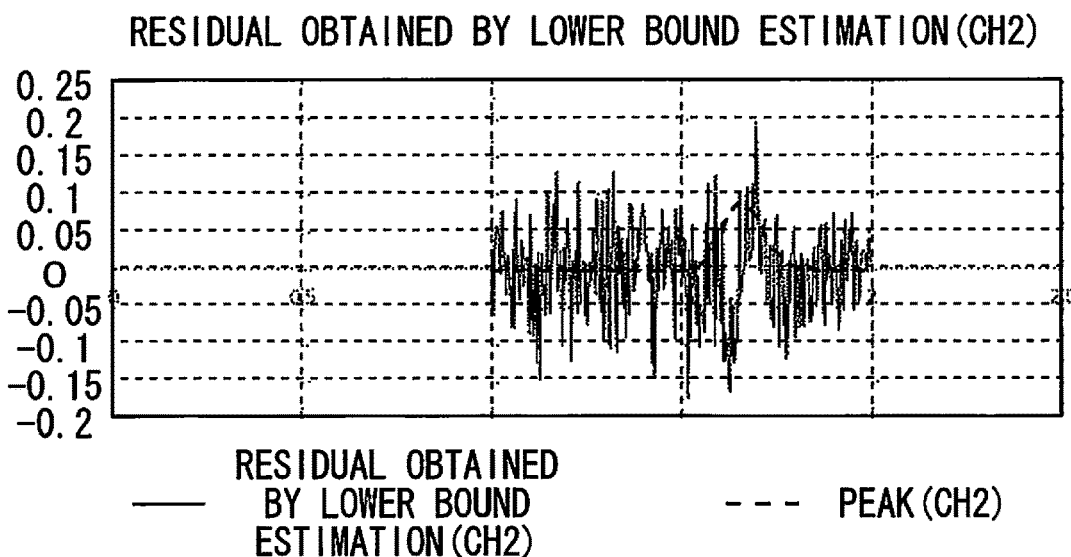
F I G. 1 3
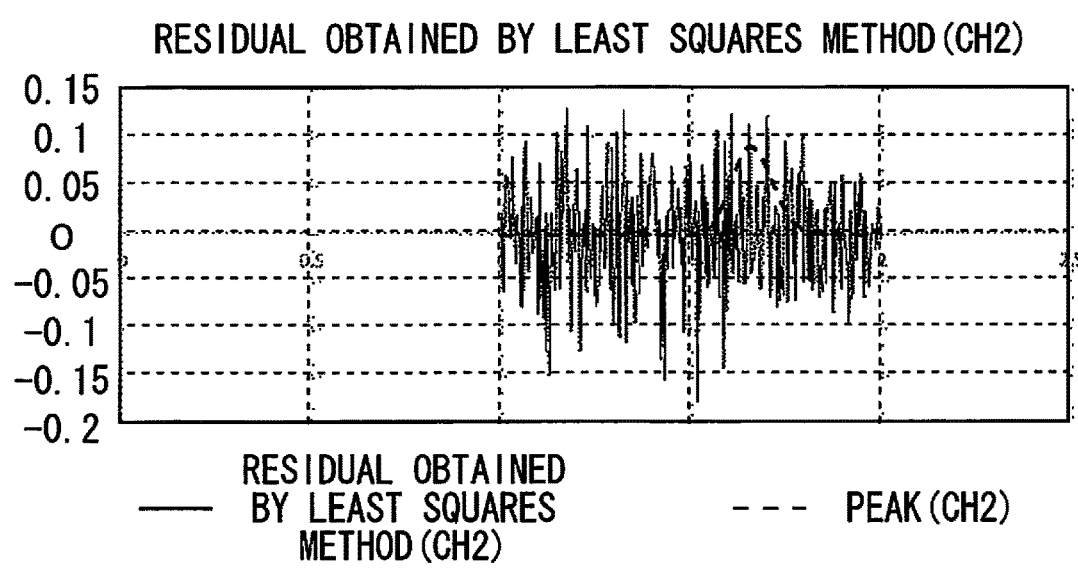

F I G.  1 4
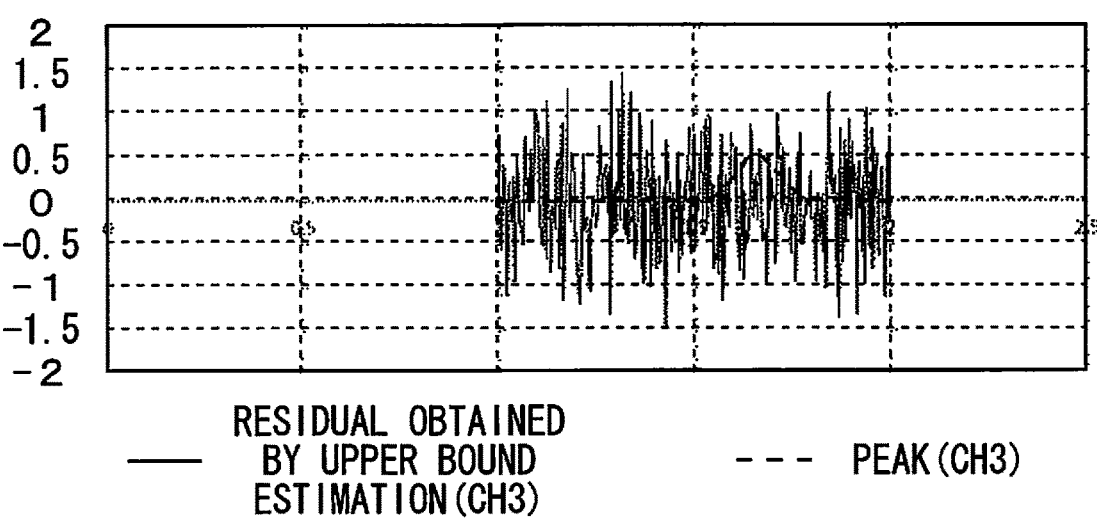
RESIDUAL OBTAINED BY UPPER BOUND ESTIMATION(CH3)
——— RESIDUAL OBTAINED BY UPPER BOUND ESTIMATION(CH3)    - - - PEAK(CH3)
F I G.  1 5
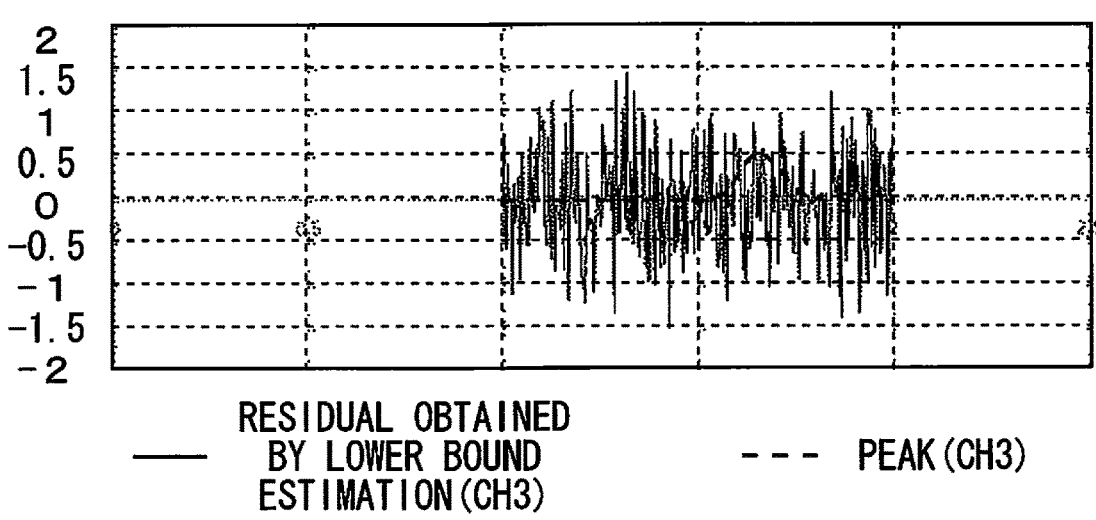
RESIDUAL OBTAINED BY LOWER BOUND ESTIMATION(CH3)
——— RESIDUAL OBTAINED BY LOWER BOUND ESTIMATION(CH3)    - - - PEAK(CH3)

F I G. 1 6
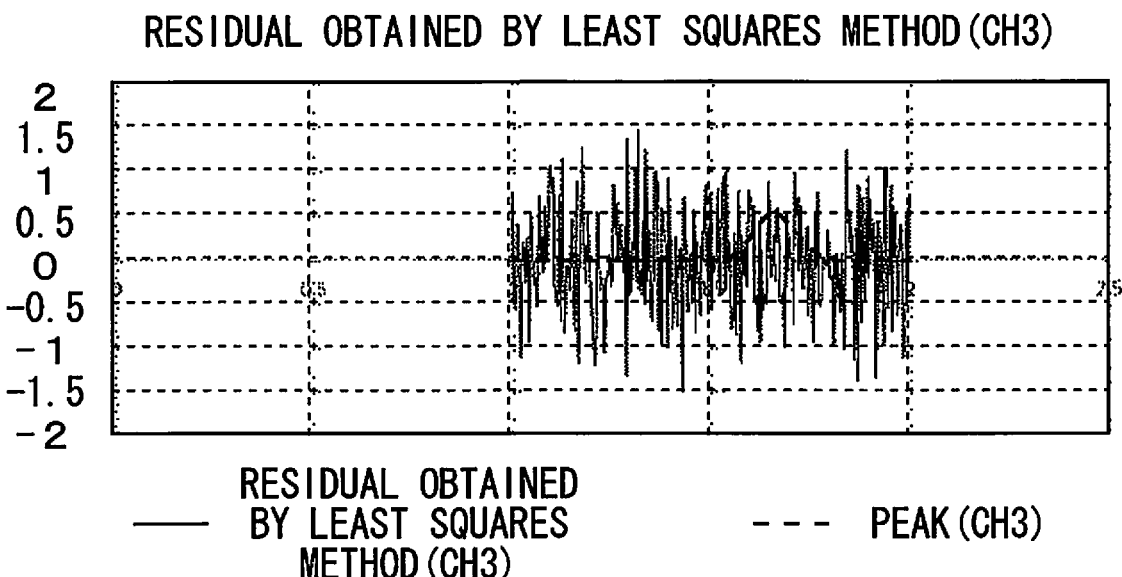
RESIDUAL OBTAINED BY LEAST SQUARES METHOD(CH3)
—— RESIDUAL OBTAINED
BY LEAST SQUARES
METHOD(CH3)
- - - PEAK(CH3)

F I G.  1 7
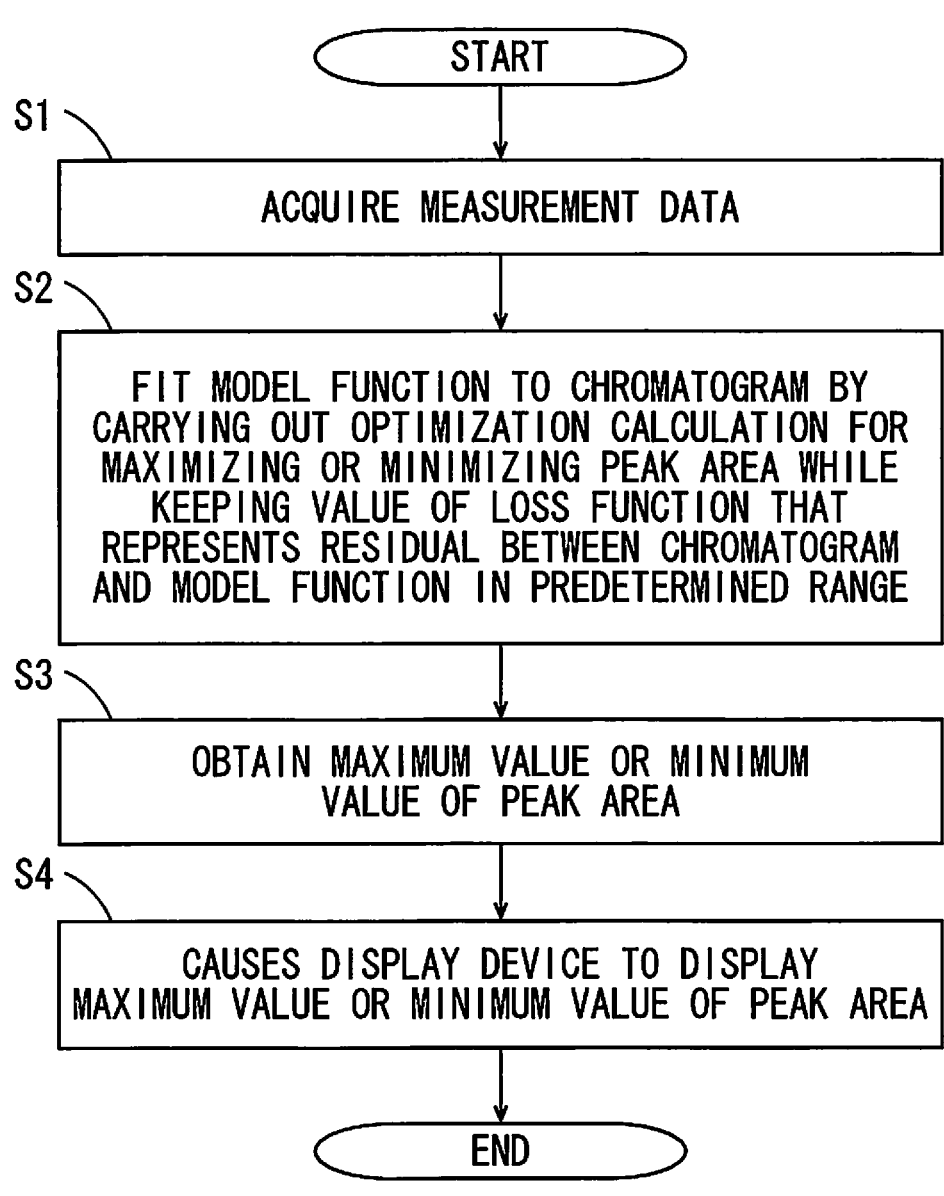

PEAK AREA DISPLAY DEVICE, PEAK AREA DISPLAY METHOD, PEAK AREA CALCULATION DEVICE AND PEAK AREA CALCULATION METHOD

BACKGROUND

Technical Field

The present invention relates to a device and a method for displaying a peak area of a measured waveform and a device and a method for calculating the peak area.

Description of Related Art

A model function is fitted to a chromatogram for a quantitative analysis and a qualitative analysis of a waveform measured by a chromatograph. It is important for a model function to be able to be fitted to an actually measured waveform with high accuracy. In "Peak Fit," of HULINKS Inc., [searched on Jun. 4, 2021], <URL: https://www.hulinks.co.jp/software/da_visual/peakfit/functions#chorom>, various model functions are suggested for a quantitative analysis and a qualitative analysis of a waveform measured by a chromatograph.

In management of a pharmaceutical product, it is required that the content of a main component included in the pharmaceutical product is equal to or larger than a prescribed amount. Further, the content of an impurity included in the pharmaceutical product is required to be equal to or smaller than a prescribed amount. Therefore, in an analysis of the pharmaceutical product, the main component and the impurity are quantitatively and qualitatively analyzed.

SUMMARY

As described above, fitting of a model function is preferred to be more approximate to an actually measured waveform. This is because an object is that the model function is to be fitted to a plausible shape representing the actually measured waveform. In contrast, in management of impurities of a pharmaceutical product, for example, it is important to manage impurities more appropriately than to fit a model function to a plausible shape. That is, it may be preferred to evaluate the upper bound or the lower bound of a peak area rather than to search for a plausible shape representing a measured waveform.

An object of the present invention is to provide a method that enables evaluation of an upper bound or a lower bound of a peak area of a specific component included in measurement data.

A peak area display device according to one aspect of the present invention includes an acquirer that acquires measurement data measured by a chromatograph, a peak area calculator that fits a model function to a chromatogram to obtain a maximum value or a minimum value of a peak area by performing optimization calculation to maximize or minimize the peak area while keeping a value to be taken by a loss function representing a residual between the chromatogram obtained from the measurement data and the model function in a predetermined range, and a display device that displays a maximum value or a minimum value of the peak area obtained by the peak area calculator, or information obtained by a process of the maximum value or the minimum value of the peak area.

A peak area calculation device according to another aspect of the present invention includes an acquirer that acquires measurement data measured by a chromatograph, and a peak area calculator that fits a model function to a chromatogram to obtain a maximum value or a minimum value of a peak area by performing optimization calculation to maximize or minimize the peak area while keeping a value to be taken by a loss function representing a residual between the chromatogram obtained from the measurement data and the model function in a predetermined range.

The present invention is also directed to a peak area display method and a peak area calculation method.

Other features, elements, characteristics, and advantages of the present disclosure will become more apparent from the following description of preferred embodiments of the present disclosure with reference to the attached drawings.

BRIEF DESCRIPTION OF THE DRAWING

FIG. 1 is a diagram showing the configuration of a peak area display device according to the present embodiment;

FIG. 2 is a block diagram showing the functions of the peak area display device according to the present embodiment;

FIG. 3 is a diagram showing a chromatogram obtained in regard to a sample;

FIG. 4 is a diagram showing a chromatogram in regard to a first main component of measurement data MD;

FIG. 5 is a diagram showing a chromatogram in regard to a second main component of the measurement data MD;

FIG. 6 is a diagram showing a chromatogram in regard to a third main component of the measurement data MD;

FIG. 7 is a diagram for comparison between an upper bound estimation area and a least squares estimation area;

FIG. 8 is a diagram showing a residual obtained by upper bound estimation in regard to CH1;

FIG. 9 is a diagram showing a residual obtained by lower bound estimation in regard to CH1;

FIG. 10 is a diagram showing a residual obtained by least squares estimation in regard to CH1;

FIG. 11 is a diagram showing a residual obtained by upper bound estimation in regard to CH2;

FIG. 12 is a diagram showing a residual obtained by lower bound estimation in regard to CH2;

FIG. 13 is a diagram showing a residual obtained by least squares estimation in regard to CH2;

FIG. 14 is a diagram showing a residual obtained by upper bound estimation in regard to CH3;

FIG. 15 is a diagram showing a residual obtained by lower bound estimation in regard to CH3;

FIG. 16 is a diagram showing a residual obtained by least squares estimation in regard to CH3;

FIG. 17 is a flowchart showing a peak area display method according to an embodiment.

DETAILED DESCRIPTION

Figure 18:
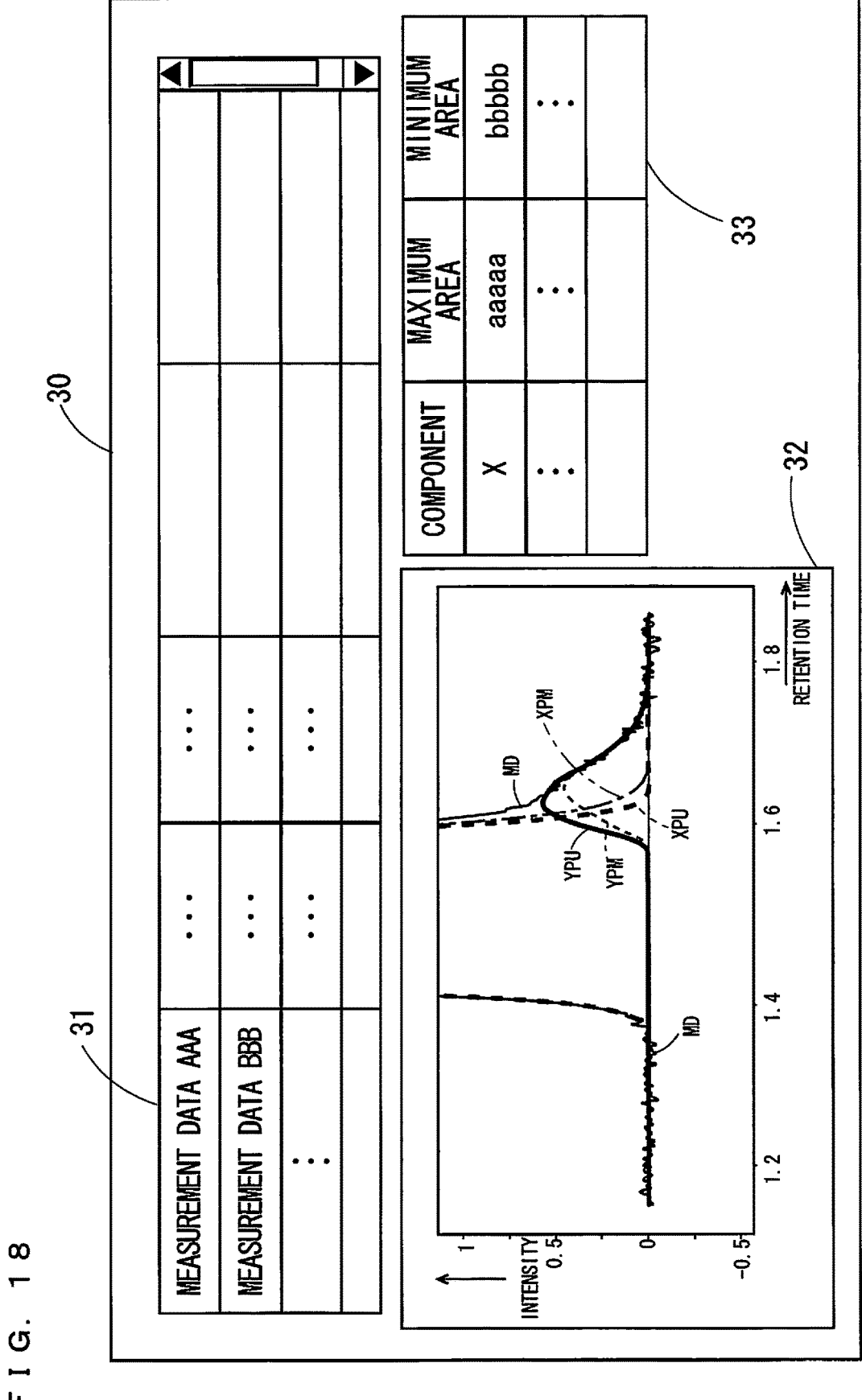
FIG. 18 is a diagram showing an estimation result screen.

A peak area display device, a peak area display method, a peak area calculation device and a peak area calculation method according to embodiments of the present invention will now be described with reference to the attached drawings.

(1) Configuration of Peak Area Display Device

FIG. 1 is a diagram showing the configuration diagram of a peak area display device 1 according to an embodiment. The peak area display device 1 of the present embodiment acquires measurement data MD of a sample obtained in a liquid chromatograph, a gas chromatograph or the like.

The peak area display device 1 of the present embodiment is constituted by a personal computer, for example. As shown in FIG. 1, the peak area display device 1 includes a CPU (Central Processing Unit) 11, a RAM (Random Access Memory) 12, a ROM (Read Only Memory) 13, an operation unit 14, a display 15, a storage device 16, a communication interface (I/F) 17 and a device interface (I/F) 18.

The CPU 11 controls the peak area display device 1 as a whole. The RAM 12 is used as a work area for execution of a program by the CPU 11. Various data, a program and the like are stored in the ROM 13. The operation unit 14 receives an input operation performed by a user. The operation unit 14 includes a keyboard, a mouse, etc. The display 15 displays information such as a result of peak fitting and a maximum value and/or a minimum value of a peak area. The storage device 16 is a storage medium such as a hard disc. A program P1, measurement data MD, an error a and display data DD are stored in the storage device 16. The program P1 executes a process of acquiring a chromatogram, a process of fitting a model function to a chromatogram, a process of obtaining a maximum value and/or a minimum value of a peak area, a process of displaying a calculated maximum value and/or a calculated minimum value of a peak area on the display 15, and the like. The communication interface 17 is an interface that communicates with another computer through wireless or wired communication. The device interface 18 is an interface that accesses a storage medium 19 such as a CD, a DVD or a semiconductor memory.

(2) Functional Configuration of Peak Area Display Device

FIG. 2 is a block diagram showing the functional configuration of the peak area display device 1. In FIG. 2, a controller 20 is a function that is implemented by execution of the program P1 by the CPU 11 while the CPU 11 uses the RAM 12 as a work area. The controller 20 includes an acquirer 21, a peak area calculator 22 and an outputter 23. That is, the acquirer 21, the peak area calculator 22 and the outputter 23 are the functions implemented by execution of the program P1. In other words, each of the functions 21 to 23 is a function included in the CPU 11.

The acquirer 21 receives measurement data MD. The acquirer 21 receives measurement data MD from another computer, an analysis device or the like via the communication interface 17, for example. Alternatively, the acquirer 21 receives measurement data MD saved in the storage medium 19 via the device interface 18.

The peak area calculator 22 executes a process of fitting a model function to a chromatogram obtained from measurement data MD and a process of calculating the maximum value and/or the minimum value of a peak area based on a result of fitting of the model function.

The outputter 23 causes the display 15 to display the maximum value and/or the minimum value of a peak area calculated by the peak area calculator 22. Further, the outputter 23 causes the display 15 to display information in regard to measurement data MD, a result of fitting of a model function carried out by the peak area calculator 22 and the like.

The program P1 is saved in the storage device 16, by way of example. In another embodiment, the program P1 may be provided in the form of being saved in the storage medium 19. The CPU 11 may access the storage medium 19 via the device interface 18 and may save the program P1 saved in the storage medium 19 in the storage device 16 or the ROM 13. Alternatively, the CPU 11 may access the storage medium 19 through the device interface 18 and may execute the program P1 saved in the storage medium 19. Alternatively, the CPU 11 may download the program P1 from a server on a network through the communication interface 17 and save the downloaded program P1 in the storage device 16 or the ROM 13.

(3) Chromatogram

The nature of a chromatogram in which peaks of a plurality of components overlap with one another will be described before description of the peak area display method of the present embodiment. FIG. 3 is a diagram showing a chromatogram obtained in regard to a sample. In this chromatogram, a peak AP1 in regard to a component A appears. The peak AP1 is a peak obtained when it is considered that tailing is occurring in a peak of the component A. In contrast, a peak AP2 is a peak obtained when it is assumed that tailing is not occurring in the peak of the component A. A residual peak RP is a peak obtained when the peak AP2 is subtracted from the peak AP1. Although it is possible to consider that the residual peak RP is tailing of the peak of the component A, it is also possible to consider that the residual peak RP is a peak derived from a peak BP of another component B. In the present embodiment, in a case in which a peak of an impurity overlaps with a peak of a main component of a pharmaceutical product, for example, it is one object to quantitatively analyze the peak of the impurity.

(4) Peak Fitting Process and Peak Area Estimation Process

Next, the peak area display method according to the embodiment will be described. In the following description, the maximum value of a peak area of an impurity included in a chromatogram is displayed on the display 15 based on measurement data MD acquired in regard to a pharmaceutical product, by way of example. In regard to the pharmaceutical product, the content of an impurity is required to be equal to or smaller than a prescribed amount. As such, with the peak area display method of the present embodiment, the maximum value of a peak area of an impurity included in the pharmaceutical product is obtained, so that the upper bound of the content of an impurity is estimated and used for the quality evaluation of the pharmaceutical product.

(4-1) Multi-Dimensional Measurement Data

Measurement data MD is multi-dimensional data acquired in regard to a pharmaceutical product to be analyzed. Here, the measurement data MD is three-dimensional data having three axes of a retention-time direction, a spectral direction (frequency direction) and an intensity, by way of example. In this case, the measurement data MD is represented as matrix data having the row corresponding to the retention-time direction, the column corresponding the spectral direction and the intensity as an element. For example, the measurement data MD is the data acquired in a liquid chromatograph including a PDA detector (photo-diode array detector).

(4-2) Dimensional Compression of Measurement Data

In pre-processing, the peak area calculator 22 compresses the dimension of a spectrum of the measurement data MD acquired by the acquirer 21. In the present embodiment, the peak area calculator 22 performs SVD dimensional compression utilizing Singular Value Decomposition (SVD). Further, the peak area calculator 22 normalizes the intensity of the dimensionally compressed measurement data MD. As a dimensional compression method, another method other than the SVD dimensional compression may be used. Needless to say, the measurement data MD does not have to be dimensionally compressed and may be processed without compression. Here, each dimension which is compressed in the spectral direction is referred to as a channel (CH).

FIGS. 4 to 6 are diagrams showing the measurement data MD compressed into three dimensions by the SVD dimensional compression. In each of FIGS. 4 to 6, the abscissa indicates a retention time, and the ordinate indicates an intensity. A chromatogram of a channel 1 (CH1) shown in FIG. 4 is the chromatogram in regard to a first main component of the measurement data MD, and a chromatogram of a channel 2 (CH2) shown in FIG. 5 is the chromatogram in regard to a second main component of the measurement data MD. A chromatogram of a channel 3 (CH3) shown in FIG. 6 is the chromatogram in regard to a third main component of the measurement data MD.

(4-3) Model Function

The peak area calculator 22 models the measurement data MD on the assumption that there are as many model functions and spectra representing the shape of a chromatogram as the number of substances. Further, the peak area calculator 22 utilizes the baseline of each of the channels CH1 to CH3 of the measurement data MD as a model obtained when a noise is added to an ideal signal represented by a linear function. As a model function representing a baseline, another polynomial or an index of polynomial may be used. Alternatively, similarly to a peak, a baseline may also be modeled as having information such as a baseline shape and a spectrum.

The peak area calculator 22 uses a GAM model with a second derivative constraint, for example, as a model function. A model function with a second derivative constraint is a model function with a constraint that a second derivative (second difference) is non-positive with respect to a logarithmic function of the model function. This is because the peak shape of a chromatogram has a characteristic that its second derivative of logarithmic function is non-positive. Further, the GAM model is a method of fitting a model function to a chromatogram using a Generalized Additive Model (GAM). For example, smoothing spline is used as the generalized additive model. However, a model function to be used by the peak area calculator 22 is not limited in particular. The peak area calculator 22 may use a generally used EMG function or BEMG function as a model function.

(4-4) Fitting of Model Function

The peak area calculator 22 fits a model function such as the one described above to the chromatograms of the channels CH1 to CH3 by a least squares method. Alternatively, the peak area calculator 22 may fit a model function with respect to the chromatograms of the channels CH1 to CH3 by calculation for the purpose of obtaining a single solution such as maximum likelihood estimation and maximum a posteriori probability. That is, the peak area calculator 22 fits a model function with respect to a chromatogram for the purpose of minimizing the value of a loss function representing the residual between the chromatogram and the model function.

The peak area calculator 22 carries out calculation to solve a constrained optimization problem in which the peak area of an impurity is maximized under a constraint condition that a value obtained when an error a is added to the minimum loss value (minimum LOSS) is the largest allowable value to be taken by a loss function. In conventional peak fitting, a parameter is determined such that a loss function takes a minimum loss value. With this peak fitting, the model function is fitted to a plausible shape also with respect to a peak of an impurity. On the other hand, because the peak area calculator 22 performs peak fitting after the error a is added to the minimum loss value, a degree of freedom is provided with respect to fitting by a value of the error a as compared to the conventional fitting. Under such a constraint condition, the peak area calculator 22 performs peak fitting such that the peak area of an impurity is maximized.

A range (predetermined range) to be taken by a loss function may be set by user input, or may be set by multiplication of an observation noise by an empirically obtained predetermined value or addition of a predetermined value to the observation noise. Further, the influence, which a noise component has on an estimated peak height, can be calculated as a normal error propagation. Thus, the error range that can be additionally generated may be obtained based on a standard error of the estimated peak height. In the present embodiment, up to a value equivalent to $3\sigma$, $\sigma$ being a standard error of a peak height, is set allowable, so that a value obtained when the sum of squares of a peak waveform of $+3\sigma$ is added to a least squares sum is set as a largest allowable value to be taken by a loss function.

The error a to be added to the minimum loss value is saved in the storage device 16 as shown in FIG. 1. The error a may be a small enough value as an estimation error. In the present embodiment, the error a is determined because it is considered that an amount of noise be propagated with respect to a peak height of an impurity obtained as the least squares solution an error to be propagated. Specifically, the error a is determined based on the consideration that a value obtained by multiplication of a standard error of a noise amount by several times is added to a loss function as an error of a peak height. The magnitude of noise is calculated based on the signal level around a peak, for example. Alternatively, the magnitude of noise may be calculated based on frequency separation such as calculation based on an n-th order difference. In this manner, although being calculated based on the level of a noise extracted from the vicinity of a peak which is an area subject to a process, the error a may be calculated based on a noise extracted from an area before or after the peak.

In this manner, the peak area calculator 22 of the present embodiment performs peak fitting so as to maximize the peak area of an impurity under a constraint condition that a value obtained when the error a is added to the minimum loss value (minimum LOSS) is the largest allowable value to be taken by the loss function. Thus, the upper bound of a value to be taken in regard to the peak area of an impurity can be evaluated. Therefore, it is possible to acquire effective information in impurity management of a pharmaceutical product.

In the above-mentioned embodiment, the model function is fitted so as to maximize the peak area of an impurity in order to manage impurities of a pharmaceutical product. In contrast, in order to manage a main component (active ingredient) of a pharmaceutical product, a model function may be fitted so as to minimize the peak area of the main component. That is, the peak area calculator 22 carries out calculation to solve a constrained optimization problem in which the peak area of a main component is minimized under a constraint condition that a value obtained when an error a is added to the minimum loss value is the smallest allowable value to be taken by a loss function. Thus, the lower bound of a value to be taken in regard to a peak area of the main component can be evaluated. Therefore, it is possible to acquire effective information in management of an active ingredient of a pharmaceutical product.

(4-5) Result of Experiment

FIG. 7 is experimental data showing a result of fitting of a model function performed by the peak area calculator 22. FIG. 7 is a diagram showing peaks of a main component X and an impurity Y of a pharmaceutical product detected with respect to measurement data MD. Peaks XPM and YPM are peaks of the main component X and the impurity Y, respectively, which are detected by a method similar to the conventional method. That is, the peaks XPM and YPM are results obtained when a model function is fitted with use of the conventional method using a least squares method. Peaks XPU and YPU are peaks of the main component X and the impurity Y, respectively, detected by the method of the present embodiment. That is, the peak YPU represents the upper bound of the peak area of the impurity Y. While the peak YPM is a result of estimation of a plausible peak in regard to the impurity Y, the peak YPU is a result of estimation presenting the upper bound of the peak area of the impurity Y.

FIGS. 8 to 16 are experimental data showing residuals obtained as a result of execution of the fitting process of the model function of the present embodiment with respect to the measurement data MD of CH1 to CH3 shown in FIGS. 4 to 6. In FIGS. 8 to 16, the abscissa indicates a retention time, and the ordinate indicates an intensity. Further, in FIGS. 8 to 16, the peak shapes of CH1 to CH3 are indicated by broken lines for reference.

FIG. 8 shows the residual between the measurement data MD of CH1 shown in FIG. 4 and a result of peak fitting obtained by upper bound estimation. The upper bound estimation is a fitting process of maximizing a peak area according to the present embodiment. FIG. 10 shows the residual between the measurement data MD of CH1 shown in FIG. 4 and a result of peak fitting performed with use of the conventional least squares method. From these results of experiments, it is found that there is no significant difference in regard to a residual also in a case in which the upper bound estimation method according to the present embodiment is performed as compared to a case in which the conventional method is performed. In this manner, it is found that the upper bound estimation method of the present embodiment realizes maximization of a peak area of an impurity while maintaining sufficient accuracy for fitting of a model function. FIG. 9 shows reference data representing the residual between the measurement data MD of CH1 shown in FIG. 4 and a result of peak fitting obtained by lower bound estimation. Lower bound estimation is a fitting process according to the present embodiment of minimizing a peak area. In this manner, it is found that there is no significant difference in regard to a residual also with the lower bound estimation method.

FIG. 11 shows the residual between the measurement data MD of CH2 shown in FIG. 5 and a result of peak fitting obtained by the upper bound estimation. FIG. 13 shows the residual between the measurement data MD of CH1 shown in FIG. 5 and a result of estimation obtained by the conventional least squares method. Similarly to CH1, it is found that there is no significant difference in regard to a residual also in the measurement data MD of CH2 as compared to the conventional method. FIG. 12 shows reference data representing the residual between the measurement data MD of CH2 shown in FIG. 5 and a result of peak fitting obtained by the lower bound estimation. It is found that there is no significant difference in regard to a residual also with the lower bound estimation method. It is found that similar results are obtained also with respect to the measurement data MD of CH3 shown in FIGS. 14 to 16.

(4-6) Peak Area Display Method

Next, the peak area display method of the present embodiment will be described with reference to the flowchart of FIG. 17. The flowchart of FIG. 17 is a process realized by execution of the program P1 by the CPU 11. In the step S1, the acquirer 21 acquires measurement data MD. The acquirer 21 saves the measurement data MD in the storage device 16. As described above, the measurement data MD is multi-dimensional data.

Next, in the step S2, the peak area calculator fits a model function to a chromatogram by performing optimization calculation for maximizing or minimizing a peak area while keeping a value that represents the residual between a chromatogram and a model function and is to be taken by a loss function in a predetermined range. In the above-mentioned embodiment, the peak area calculator 22 uses an error a saved in the storage device 16, and performs peak fitting so as to maximize the peak area of an impurity under a constraint condition that a value obtained when the error a is added to the minimum loss value is the largest allowable value to be taken by the loss function. Then, in the step S3, the peak area calculator 22 obtains the maximum value or the minimum value of the peak area of a target component based on a result of fitting in the step S2. For example, the peak area calculator 22 obtains the maximum value of the peak area of an impurity contained in a pharmaceutical product. As shown in FIG. 2, the peak area calculator 22 saves display data DD including the calculated maximum value and/or the calculated minimum value of the peak area in the storage device 16.

Then, in the step S4, the outputter 23 acquires the display data DD from the storage device 16 and displays the display data DD on the display 15. FIG. 18 is a diagram showing one example of an estimation result screen 30 displayed on the display 15. The estimation result screen 30 includes a data display area 31, a chromatogram display area 32 and a peak-area display area 33. A list of the measurement data MD is displayed in the data display area 31. When any of the measurement data MD is selected in the data display area 31, result of fitting of the model function corresponding to the selected measurement data MD is displayed in the chromatogram display area 32.

In the peak-area display area 33, the maximum area (upper bound) and/or the minimum area (lower bound) of a peak displayed in the chromatogram display area 32 is displayed. The user can confirm the maximum value (upper bound) of the peak area of an impurity contained in a pharmaceutical product while confirming the validity of a result of fitting of a peak displayed in the chromatogram display area 32. Alternatively, the user can confirm the minimum value (lower bound) of the peak area of an active ingredient contained in the pharmaceutical product.

(5) Modified Examples

In the above-mentioned embodiment, the peak area calculator 22 uses the constraint condition that a value obtained when the error a is added to the minimum loss value is the largest allowable value to be taken by the loss function. In another embodiment, the peak area calculator 22 may solve a loss function minimization problem with regularization in which the value of a peak area is added as a penalty term.

In order to maximize the peak area of an impurity, the peak area may be added as a negative value in a penalty term. With this method, the strength of regularization may be adjusted after the value of a loss function is acquired.

In the above-mentioned embodiment, the measurement data MD is three-dimensional data acquired from a liquid chromatograph including a PDA detector, by way of example. In another example, the measurement data MD may be three-dimensional data acquired in a scan mode of a liquid chromatography-mass spectrometer. In this case, the measurement data MD is three-dimensional data having three axes of a retention time, a mass spectrum and an intensity.

Description has been made in regard to the peak area display device 1 that displays the maximum value and/or the minimum value of a peak area on the display 15. In another embodiment, the device and method of the above-mentioned embodiment may be used as a peak area calculation device that calculates the maximum value and/or the minimum value of a peak area. The peak area calculation device can store the maximum value of a peak area of an impurity of a pharmaceutical product, for example, in a storage medium as evaluation data of the pharmaceutical product.

In the above-mentioned embodiment, the maximum value and/or the minimum value of a peak area is exemplified as the display data DD. In another example, the display data DD may be the information obtained by a process of the maximum value or the minimum value. Specifically, in a case in which the maximum value or the minimum value is obtained in regard to two or more peak areas, it may be the ratio between the maximum value (or the minimum value) of a first peak and the maximum value (or the minimum value) of a second peak.

(6) Aspects

It will be appreciated by those skilled in the art that the exemplary embodiments described above are illustrative of the following aspects.
(Item 1)
A peak area display device according to one aspect includes an acquirer that acquires measurement data measured by a chromatograph, a peak area calculator that fits a model function to a chromatogram to obtain a maximum value or a minimum value of a peak area by performing optimization calculation to maximize or minimize the peak area while keeping a value to be taken by a loss function representing a residual between the chromatogram obtained from the measurement data and the model function in a predetermined range, and a display device that displays a maximum value or a minimum value of the peak area obtained by the peak area calculator, or information obtained by a process of the maximum value or the minimum value of the peak area.

With this peak area display device, it is possible to evaluate the upper bound or the lower bound of a peak area of a specific component included in measurement data.
(Item 2)
The peak area display device according to item 1, wherein the measurement data may be data obtained by an analysis process of a pharmaceutical product, and the peak area calculator may obtain a maximum value of a peak area of an impurity included in the pharmaceutical product.

It is possible to manage impurities included in a pharmaceutical product. Thus, it is possible to provide useful information for performance evaluation of a pharmaceutical product.
(Item 3)
The peak area display device according to item 1 or 2, wherein the optimization calculation may include calculation for solving a constrained optimization problem in which the peak area is maximized or minimized under a constraint condition that a value obtained when a predetermined value is added to a minimum loss value is a largest allowable value to be taken by the loss function.

It is possible to maximize or minimize a peak area while providing a degree of freedom to the accuracy of peak fitting by providing a range to a value to be taken by a loss function.
(Item 4)
The peak area display device according to item 1, wherein the optimization calculation may include calculation for solving a loss function minimization problem with regularization in which a value of the peak area is a penalty term.

It is possible to perform peak fitting while maximizing or minimizing a peak area.
(Item 5)
The peak area display device according to any one of items 1 to 4, wherein the loss function may include a function that acquires a residual between the chromatogram and the model function using a least squares method.

It is possible to fit a model function to a chromatogram.
(Item 6)
The peak area display device according to any one of items 1 to 4, wherein the loss function may include a function that acquires a residual between the chromatogram and the model function using maximum likelihood estimation and maximum a posterior probability.

It is possible to fit a model function to a chromatogram.
(Item 7)
A peak area calculation device according to another aspect includes an acquirer that acquires measurement data measured by a chromatograph, and a peak area calculator that fits a model function to a chromatogram to obtain a maximum value or a minimum value of a peak area by performing optimization calculation to maximize or minimize the peak area while keeping a value to be taken by a loss function representing a residual between the chromatogram obtained from the measurement data and the model function in a predetermined range.

With this peak area calculation device, it is possible to acquire the upper bound or the lower bound of a peak area of a specific component included in the measurement data.
(Item 8)
The peak area calculation device according to item 7, wherein the measurement data may be data obtained by an analysis process of a pharmaceutical product, and the peak area calculator may obtain a maximum value of a peak area of an impurity included in the pharmaceutical product.

It is possible to manage impurities included in a pharmaceutical product. Thus, it is possible to provide useful information for performance evaluation of a pharmaceutical product.

(Item 9)

A peak area display method according to another aspect includes acquiring measurement data measured by a chromatograph, fitting a model function to a chromatogram to obtain a maximum value or a minimum value of a peak area by performing optimization calculation to maximize or minimize the peak area while keeping a value to be taken by a loss function representing a residual between the chromatogram obtained from the measurement data and the model function in a predetermined range, and displaying a maximum value or a minimum value of the peak area, or information obtained by a process of the maximum value or the minimum value of the peak area.

With this peak area display method, it is possible to evaluate the upper bound or the lower bound of a peak area of a specific component included in the measurement data.

(Item 10)

A peak area calculation method according to another aspect includes acquiring measurement data measured by a chromatograph, and fitting a model function to a chromatogram to obtain a maximum value or a minimum value of a peak area by performing optimization calculation to maximize or minimize the peak area while keeping a value to be taken by a loss function representing a residual between the chromatogram obtained from the measurement data and the model function in a predetermined range.

With this peak area calculation method, it is possible to acquire the upper bound or the lower bound of a peak area of a specific component included in the measurement data.

While preferred embodiments of the present disclosure have been described above, it is to be understood that variations and modifications will be apparent to those skilled in the art without departing the scope and spirit of the present disclosure. The scope of the present disclosure, therefore, is to be determined solely by the following claims.

I claim:

1. A peak area displaying device comprising:
an acquirer that acquires measurement data measured by a chromatograph;
a peak area calculator that fits a model function to a chromatogram to obtain a maximum value or a minimum value of a peak area by performing optimization calculation to maximize or minimize the peak area calculated based on the model function while keeping a value to be taken by a loss function representing a residual between the chromatogram obtained from the measurement data and the model function in a predetermined range; and
a display that displays a maximum value or a minimum value of the peak area obtained by the peak area calculator, or processed data obtained derived from the maximum value or the minimum value of the peak area,
wherein the peak area calculator is configured to:
calculate a minimum loss value representing the residual between the chromatogram and the model function,
set a predetermined range between the minimum loss value and a value obtained by adding a predetermined value to the minimum loss value, and
calculate the maximum value or the minimum value of the peak area by varying a parameter of the model function under a constraint condition that the residual between the chromatogram and the model function is within the predetermined range.

2. The peak area display device according to claim 1, wherein
the measurement data is obtained by an analysis process of a pharmaceutical product, and the peak area calculator obtains a maximum value of a peak area of an impurity included in the pharmaceutical product.

3. The peak area display device according to claim 1, wherein
the optimization calculation includes calculation for solving a constrained optimization problem in which the peak area is maximized or minimized under a constraint condition that a value obtained as a result of the predetermined value being added to the minimum loss value is a maximum allowable value to be taken by the loss function.

4. The peak area display device according to claim 1, wherein
the optimization calculation includes calculation for solving a loss function minimization problem with regularization in which a value of the peak area is a penalty term.

5. The peak area display device according to claim 1, wherein
the loss function includes a function that acquires the residual between the chromatogram and the model function using a least squares method.

6. The peak area display device according to claim 1, wherein
the loss function includes a function that acquires the residual between the chromatogram and the model function using maximum likelihood estimation and maximum a posterior probability.

7. The peak area display device according to claim 1, wherein the predetermined value is an error value.

8. A peak area calculation device comprising:
an acquirer that acquires measurement data measured by a chromatograph; and
a peak area calculator that fits a model function to a chromatogram to obtain a maximum value or a minimum value of a peak area by performing optimization calculation to maximize or minimize the peak area calculated based on the model function while keeping a value to be taken by a loss function representing a residual between the chromatogram obtained from the measurement data and the model function in a predetermined range,
wherein the peak area calculator is configured to:
calculate a minimum loss value representing the residual between the chromatogram and the model function,
set a predetermined range between the minimum loss value and a value obtained by adding a predetermined value to the minimum loss value, and
calculate the maximum value or the minimum value of the peak area by varying a parameter of the model function under a constraint condition that the residual between the chromatogram and the model function is within the predetermined range.

9. The peak area calculation device according to claim 8, wherein
the measurement data is data obtained by an analysis process of a pharmaceutical product, and the peak area calculator obtains a maximum value of a peak area of an impurity included in the pharmaceutical product.

10. The peak area calculation device according to claim 8, wherein the predetermined value is an error value.

11. A peak area display method including:

acquiring measurement data measured by a chromatograph;

fitting a model function to a chromatogram to obtain a maximum value or a minimum value of a peak area by performing optimization calculation to maximize or minimize the peak area while keeping a value to be taken by a loss function representing a residual between the chromatogram obtained from the measurement data and the model function in a predetermined range; and displaying a maximum value or a minimum value of the peak area, or information obtained by a process of the maximum value or the minimum value of the peak area.

12. A peak area calculation method including:

acquiring measurement data measured by a chromatograph; and fitting a model function to a chromatogram to obtain a maximum value or a minimum value of a peak area by performing optimization calculation to maximize or minimize the peak area calculated based on the model function while keeping a value to be taken by a loss function representing a residual between the chromatogram obtained from the measurement data and the model function in a predetermined range, wherein the performing of the optimization calculation comprises:

calculating a minimum loss value representing the residual between the chromatogram and the model function, setting a predetermined range between the minimum loss value and a value obtained by adding a predetermined value to the minimum loss value, and calculating the maximum value or the minimum value of the peak area by varying a parameter of the model function under a constraint condition that the residual between the chromatogram and the model function is within the predetermined range.

13. The peak area calculation method according to claim 12, wherein the predetermined value is an error value.

* * * * *